United States Patent
Agee et al.

(10) Patent No.: US 9,968,240 B2
(45) Date of Patent: May 15, 2018

(54) METHOD AND APPARATUS FOR TREATMENT OF CTS USING ENDOSCOPIC CARPAL TUNNEL RELEASE

(71) Applicant: JOHN M. AGEE AND KAREN K. AGEE, TRUSTEES OF THE JOHN M. AGEE TRUST, Sacramento, CA (US)

(72) Inventors: John M. Agee, Cameron Park, CA (US); Jeffrey Woodhouse, Sacramento, CA (US); Ben C. Goss, Athens, GA (US)

(73) Assignee: JOHN M. AGEE AND KAREN K. AGEE, TRUSTEES OF THE JOHN M. AGEE TRUST, Sacramento, CA (US)

( * ) Notice: Subject to any disclaimer, the term of this patent is extended or adjusted under 35 U.S.C. 154(b) by 455 days.

(21) Appl. No.: 14/705,637

(22) Filed: May 6, 2015

(65) Prior Publication Data

US 2015/0320436 A1    Nov. 12, 2015

Related U.S. Application Data

(60) Provisional application No. 61/989,278, filed on May 6, 2014.

(51) Int. Cl.
  *A61B 17/32* (2006.01)
  *A61B 1/00* (2006.01)
  *A61B 17/00* (2006.01)
(52) U.S. Cl.
  CPC ...... *A61B 1/00087* (2013.01); *A61B 1/00135* (2013.01); *A61B 17/320036* (2013.01); *A61B 2017/00296* (2013.01)

(58) Field of Classification Search
  CPC ........ A61B 17/320036; A61B 1/00087; A61B 1/00135; A61B 2017/00296
  See application file for complete search history.

(56) References Cited

U.S. PATENT DOCUMENTS

| 4,819,620 A | * | 4/1989 | Okutsu .............. A61B 1/00154 600/104 |
| 5,089,000 A | * | 2/1992 | Agee .............. A61B 17/320036 606/170 |
| 5,306,284 A |   | 4/1994 | Agee et al. |
| 5,499,992 A |   | 3/1996 | Meade et al. |
| 5,507,751 A | * | 4/1996 | Goode ................. A61B 17/221 604/264 |

(Continued)

FOREIGN PATENT DOCUMENTS

EP    03080258 B1    6/1994

OTHER PUBLICATIONS

Korean Intellectual Property Office, International Search Report and Written Opinion, PCT International Application No. PCT/US2015/029497, dated Aug. 3, 2015 (pp. 1-16), with claims searched (pp. 17-22), counterpart to U.S. Appl. No. 14/705,637 herein.

*Primary Examiner* — Timothy J Neal
(74) *Attorney, Agent, or Firm* — O'Banion & Ritchey LLP; John P. O'Banion

(57) ABSTRACT

An apparatus and method for performing endoscopic carpal tunnel release (ECTR) surgery, thereby decreasing the pressure within the carpal tunnel that impairs median nerve function.

16 Claims, 17 Drawing Sheets

(56) References Cited

U.S. PATENT DOCUMENTS

| | | | | |
|---|---|---|---|---|
| 5,549,623 A | * | 8/1996 | Sharpe | A61B 17/320016 600/564 |
| 5,569,283 A | * | 10/1996 | Green | A61B 17/320036 30/162 |
| 7,628,798 B1 | * | 12/2009 | Welborn | A61B 17/320036 606/170 |
| 7,780,690 B2 | | 8/2010 | Rehnke | |
| 7,918,784 B2 | | 4/2011 | Wellborn et al. | |
| 2008/0200758 A1 | | 8/2008 | Orbay et al. | |
| 2012/0016398 A1 | * | 1/2012 | Strickland | A61B 17/320036 606/170 |

* cited by examiner

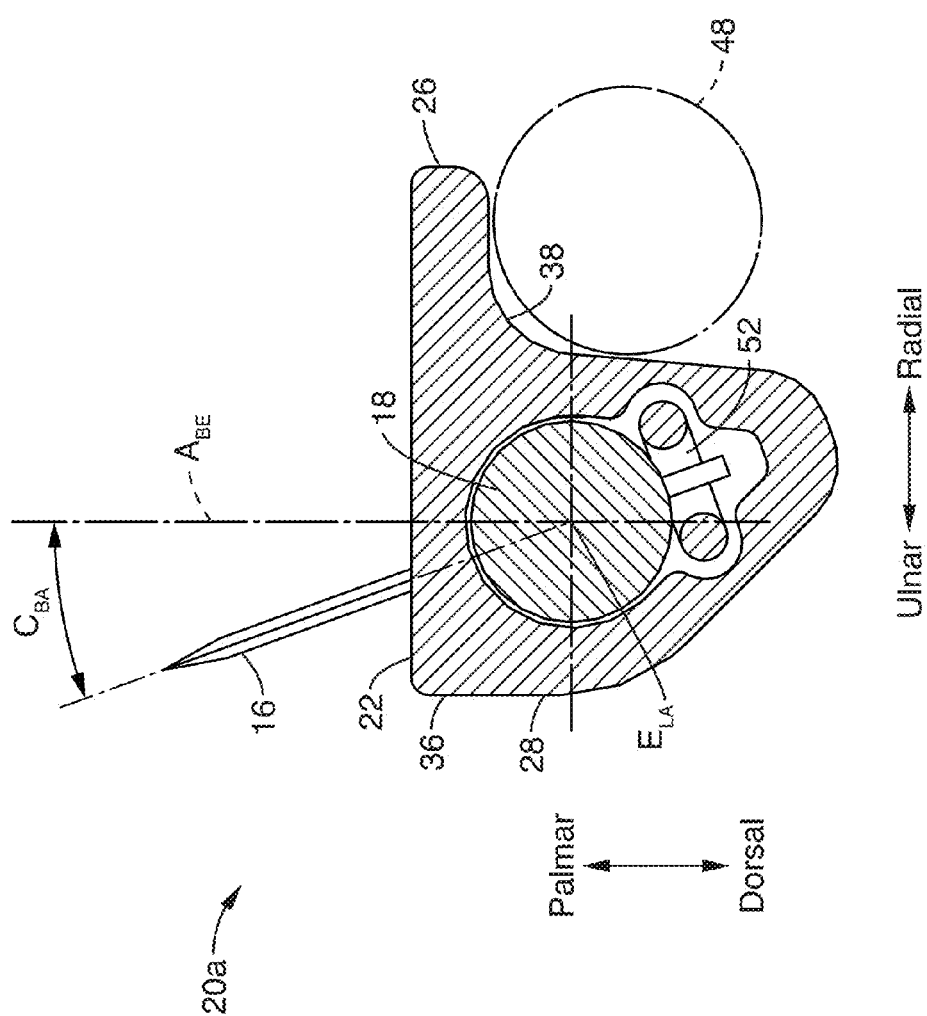

METHOD AND APPARATUS FOR TREATMENT OF CTS USING ENDOSCOPIC CARPAL TUNNEL RELEASE

CROSS-REFERENCE TO RELATED APPLICATIONS

This application claims priority to, and the benefit of, U.S. provisional patent application Ser. No. 61/989,278 filed on May 6, 2014, incorporated herein by reference in its entirety. This application is related to U.S. provisional patent application Ser. No. 61/773,320 filed on Mar. 6, 2013 and U.S. non-provisional patent application Ser. No. 14/199,902 filed on Mar. 6, 2014, both incorporated herein by reference in their entirety.

BACKGROUND

1. Technical Field

This description pertains generally to treatment of carpal tunnel syndrome and more particularly to both a method and apparatus for treatment by inserting a surgical instrument with a probe into the carpal tunnel and dividing the flexor retinaculum.

2. Background Discussion

Carpal tunnel syndrome (CTS) is a disease that refers to numerous clinical signs and symptoms resulting from an increase in pressure on the median nerve within the carpal tunnel. The increased pressure often compresses the median nerve, compromising its blood flow, resulting in the pain, numbness, and tingling characteristic of this disease. At present, it is the most widespread occupational health hazard in the industrial world. Billions of dollars are spent each year in lost working time and in the diagnosis and treatment of this syndrome.

Although the underlying cause of CTS is unknown, the treatment for CTS is well established. Non-operative treatments, including splinting, anti-inflammatory medications, and cortisone injections into the carpal tunnel, are often used initially to provide temporary relief of the symptoms. When non-operative treatments fail, the most effective treatment for CTS is surgical division of the flexor retinaculum (often called transverse carpal ligament). Surgical division of the flexor retinaculum causes the divided edges of the ligament to retract; creating a decrease in pressure within the carpal tunnel and restoring normal blood flow to the median nerve, thereby relieving the signs and symptoms of CTS. While various techniques exist for releasing the flexor retinaculum, the two most commonly used are referred to as open and endoscopic carpal tunnel release.

During an open release, a longitudinal incision is made through the skin in the palm and heel of the hand and carried down through the subcutaneous fat, palmar fascia, palmar brevis muscle, and finally through the flexor retinaculum. Once the flexor retinaculum is divided, the skin overlying the divided ligament is closed with conventional sutures and the wrist is frequently splinted until the wound heals. A typical surgery requires approximately 15 minutes to 30 minutes and is performed as an outpatient procedure.

For one existing technique called endoscopic carpal tunnel release (ECTR), various surgical instruments exist to perform division of the flexor retinaculum from within the carpal tunnel. For example, U.S. Pat. Nos. 4,963,147; 4,962,770; 5,089,000; 5,306,284; 7,628,798; 7,780,690; 7,918,784; 8,523,891 and 8,523,892 describe various surgical instruments that are used for ECTR surgery.

Current ECTR techniques that divide the flexor retinaculum from within the carpal tunnel offer certain advantages over the open technique. Patients have less post-operative morbidity which is defined by: a) less post-operative pain, especially with hand use; b) less weakness of grasp and pinch; c) less need for narcotics post-operatively; and d) an earlier return to activities of daily living and gainful employment.

Although advantages of current ECTR techniques have been well documented, debate still exists over whether ECTR is as safe as open release. The main objection to ECTR is the potential for injury to the median nerve. Even though the surgeon should have a direct and clear endoscopic view of the cutting blade and flexor retinaculum, injuries to the median nerve still occur. Because the cutting blade is elevated within the carpal tunnel, it may not cut only the flexor retinaculum, but may also cut the median nerve that also traverses through the carpal tunnel. Reasons for injury to the median nerve include surgeon inexperience, anatomic anomalies, inappropriate dissection techniques, anesthetic application method, forceful insertion of the endoscopic device into the carpal tunnel, poor visibility resulting from either local anesthesia infiltrate, fogging of the endoscopic lens, or excess synovial fluid, and patient movement.

Currently, all endoscopic surgical instruments that are designed for, intended for, and cleared by the U.S. Food & Drug Administration for treating CTS are inserted into the carpal tunnel to cut the flexor retinaculum from its deep to superficial surfaces. Therefore, this risk of injury to the median nerve is inherent in each of these endoscopic surgical methods.

Accordingly, an object of the present description is a surgical method and apparatus that offers the reduced post-operative morbidity advantages associated with ECTR, but reduces the risks that are inherent with current surgical instruments that cut the flexor retinaculum from within the carpal tunnel.

BRIEF SUMMARY

The present description includes both a method and apparatus for viewing and dividing the flexor retinaculum using an endoscopic surgical instrument that is inserted into the carpal tunnel, thereby decreasing the pressure within the carpal tunnel that impairs median nerve function.

In one aspect of the present description, a surgical method includes inserting a probe with a cutting blade of an ECTR device under the flexor retinaculum with a radial surface of the probe positioned adjacent the median nerve in the patient's carpal tunnel. With the probe in position and the endoscope viewing the deep side of the flexor retinaculum through the aperture of the probe, the median nerve is adjacent the radial and/or dorsal side of the probe, safely away from the aperture. This relationship exists just prior to the surgeon elevating the cutting blade through the aperture to initiate cutting of the flexor retinaculum.

In many cases, the patient is under some level of sedation and/or anesthesia, but remains alert enough to move and/or withdraw their hand. With this decreased level of consciousness, if a patient experiences either something uncomfortable or sudden pain, the patient may instinctively pull back their hand. This instinctive withdrawal response that often includes finger flexion, with or without wrist flexion, forearm pronation, and elbow flexion, is similar to that of an older infant's startle reflex response.

It is during a patient's response to pain that a mechanism for injury to the median nerve is increased. As the patient pronates their forearm, it may cause the median nerve to translate toward the aperture of the probe. Both finger flexion and wrist flexion are known to increase the pressure within the carpal tunnel. This increased pressure may act to force the more compliant median nerve over the radial edge of the probe and into the aperture that houses the cutting blade. If the cutting blade is either already elevated or in the process of being elevated, then an increase in the potential for injury to the median nerve exists, especially if the surgeon is beginning to pull the blade assembly proximally to initiate cutting of the flexor retinaculum.

The increase in pressure that exists within the carpal tunnel provides the driving force to translate the median nerve across the aperture of the probe. Because the aperture of the probe has a direct internal path along its longitudinal length to the ambient pressure inside the operating room, a pressure gradient often exists between the aperture inside the carpal tunnel (higher pressure) and the ambient pressure within the operating room (lower pressure). This pressure gradient causes the tissues within the patient's carpal tunnel, specifically the median nerve, to be forced into the aperture where the cutting blade resides.

Therefore, a probe of the present disclosure that includes one or more design features that minimize the pressure gradient, impedes the tendency of the median nerve to easily translate across the radial side of the aperture of the probe, and positions the elevation arc of the cutting blade in a more ulnar position would reduce the risk of injury to the median nerve.

In one embodiment, the apparatus includes: (a) a hand piece, with or without a pistol grip; (b) a probe assembly with an aperture, which has a ledge on its radial side that is designed to impede translation of the median nerve ulnarwardly over its radial side and into the aperture through which a cutting blade elevates; (c) a pressure block that separates the higher pressure inside the patient's carpal tunnel from the lower pressure outside of the patient's hand; (d) a cutting blade housed within the probe assembly; (e) a blade operating mechanism for elevating the blade into a cutting position at an angle that is inclined toward the ulnar side of the aperture, advancing the blade through the flexor retinaculum, and returning the blade to its concealed, and therefore safer non-cutting position; and (f) an endoscope for viewing the flexor retinaculum through the aperture.

Further aspects of the description will be brought out in the following portions of the specification, wherein the detailed description is for the purpose of fully disclosing preferred embodiments of the description without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 4A is a transverse cross-sectional view of the probe shown in FIG. 2.

DETAILED DESCRIPTION OF INVENTION

Referring more specifically to the drawings, for illustrative purposes the present description is embodied in the apparatus generally shown in FIG. 1 through FIG. 15. It will be appreciated that the apparatus may vary as to configuration and as to details of the parts, and that the method may vary as to the specific steps and sequence, without departing from basic concepts as disclosed herein.

FIG. 1 through FIG. 15 detail methods and apparatus for dividing the flexor retinaculum to treat and relieve the signs and symptoms of CTS. In a preferred embodiment, an improved endoscopic surgical instrument is inserted into the patient's carpal tunnel to perform cutting of the flexor retinaculum. The palmar and dorsal directions shown in FIG. 1 through FIG. 15 refer to the standard anatomical directions for the palmar and dorsal surfaces of the hand. The proximal and distal directions shown in FIG. 1 through FIG. 15 refer to the standard anatomical directions for proximal and distal of the upper extremity. The radial and ulnar directions shown in FIG. 1 through FIG. 15 refer to the standard anatomical directions for the radial and ulnar sides of the hand.

Figure 1:
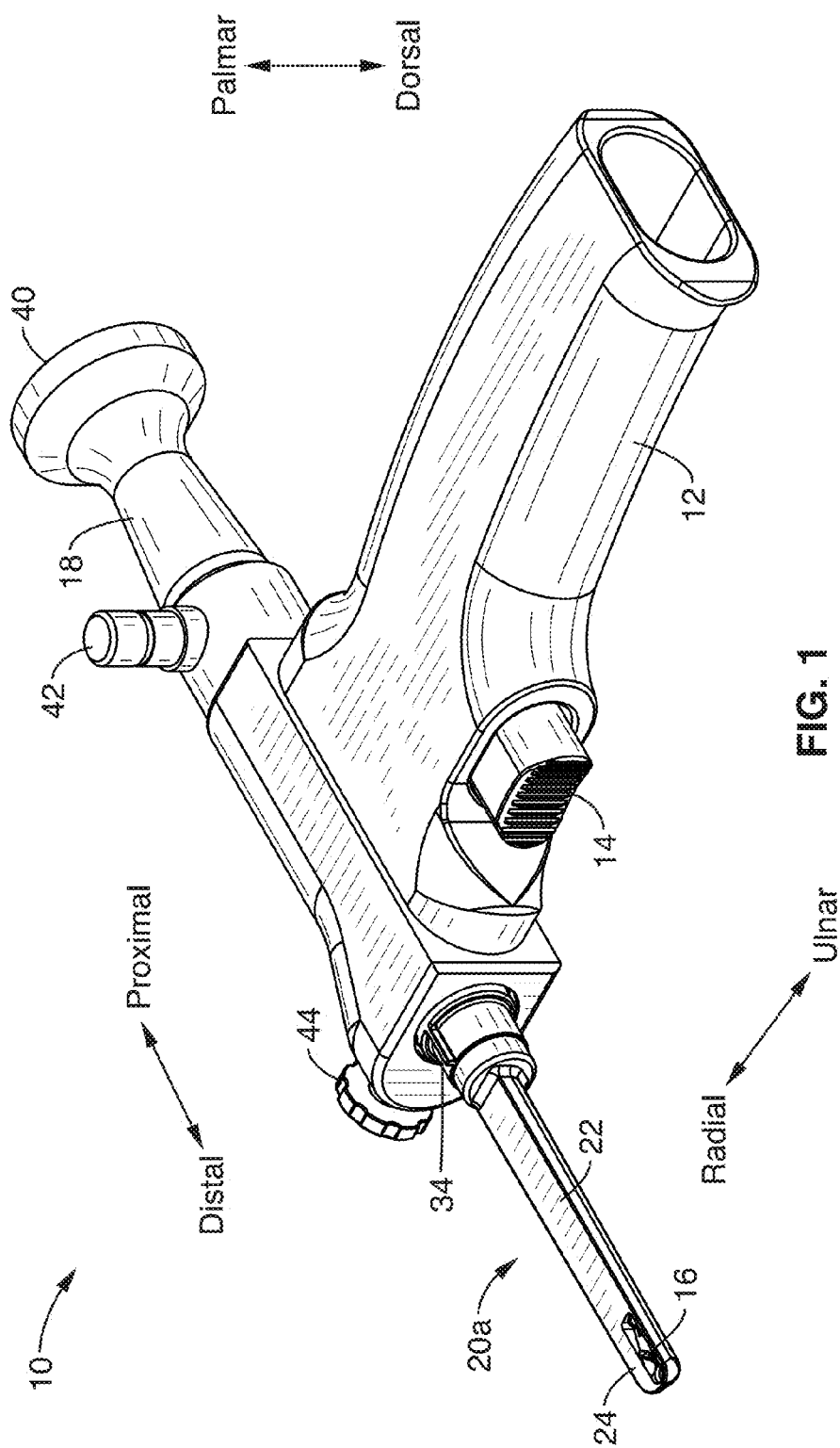
FIG. 1 is a perspective view of an endoscopic surgical instrument for performing ECTR using a cutting blade for elevation in a palmar-ulnar direction and a radial ledge, for use on the right hand of a patient during ECTR.
Figure 2:
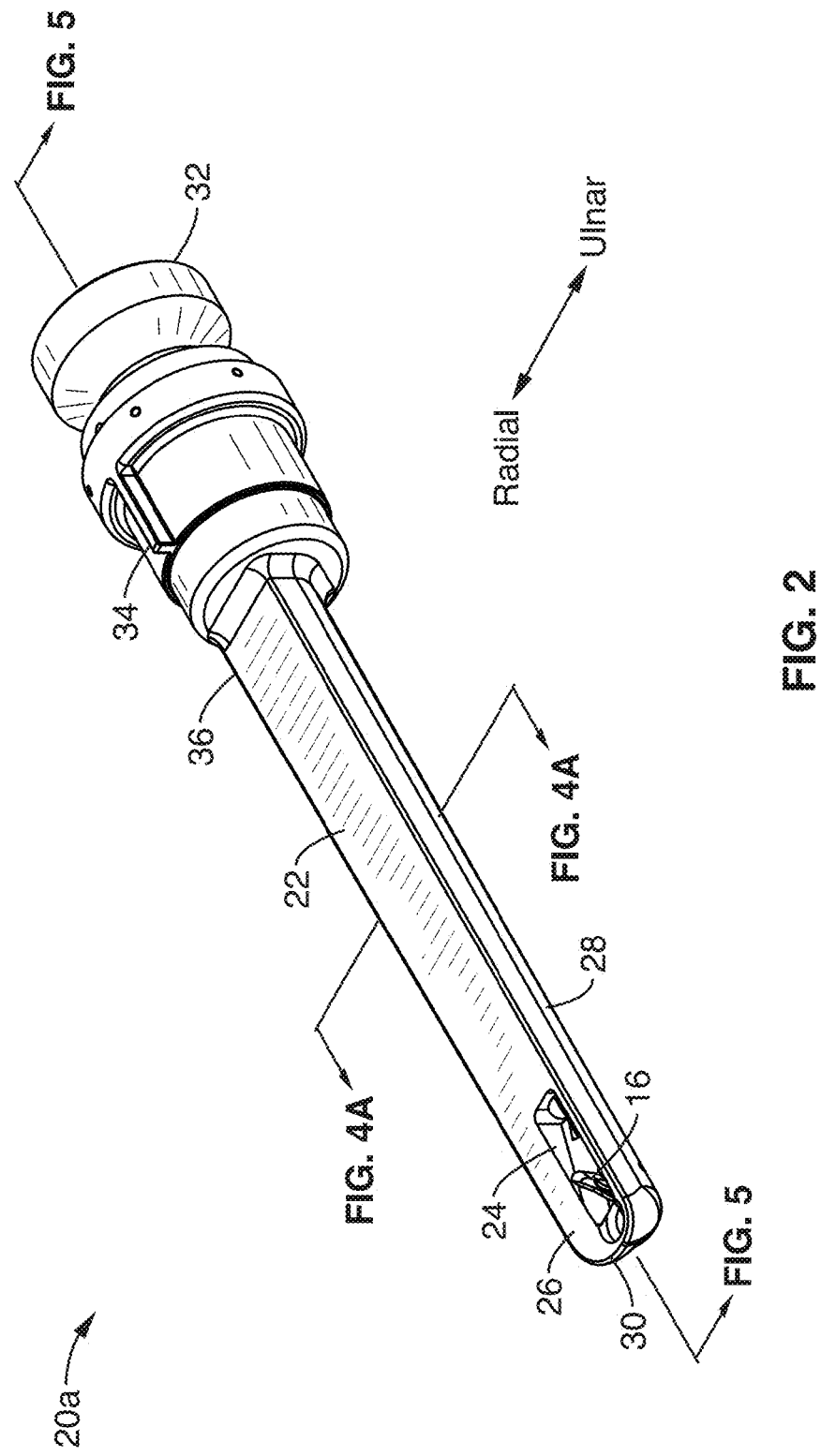
FIG. 2 is an exploded perspective view of the probe of FIG. 1.

FIG. 1 and FIG. 2 show one embodiment of an endoscopic surgical instrument 10 according to the description for dividing the flexor retinaculum. In the embodiment shown, the endoscopic surgical instrument 10 comprises a hand piece 12, an endoscope 18, and a blade assembly 20a that includes an elongate probe body 36, a cutting blade 16, and a blade operating mechanism 52 (shown in more detail with reference to FIG. 5). The endoscope 18 preferably comprises a standard size endoscope that is detachably received by the hand piece 12.

With the endoscope 18 inserted into the hand piece 12, a light source attachment connector 42 on the endoscope 18 is oriented in the palmar direction. This orientation for the light source attachment connector 42 is ideal for avoiding interference with the patient's hand and forearm.

At the proximal end of the endoscope 18 is a standard video camera attachment connector 40. At the distal end of the endoscope is the viewing lens 54 (shown in FIG. 5) that terminates near the proximal end of aperture 24. Aperture 24 and cutting blade 16 are preferably positioned at distal end 30 of the probe body 36, and biased toward the unlar side 28 of the probe 36.

In an alternative embodiment, the endoscope 18 may be replaced with an image sensor (not shown) that is mounted near the proximal end of the aperture 24 and connected to an externally mounted digital imaging device (not shown) coupled at connector 40.

The blade assembly 20a is preferably sterilizable, single use and is detachably received by the hand piece 12 using a thumbscrew 44. At the distal end of the probe 36 is an aperture 24 on its palmar side that enables viewing of the deep surface of the flexor retinaculum. Additionally, the aperture 24 permits the cutting blade 16 to elevate beyond the palmar surface 22 of the probe 36 upon operation of the blade elevation trigger 14 by the surgeon. With the blade elevation trigger 14 released, the cutting blade 16 resides safely within the aperture 24 where it cannot cut the surrounding soft tissue structures within the patient's wrist or hand.

The palmar surface 22 preferably comprises a flat or planar surface as illustrated in FIG. 1 through FIG. 5. However, it is appreciated that other variations are contemplated. For example, the palmar surface 22 may have a slight concavity or roughened surface for retaining or centering the flexor retinaculum in a set position while performing endoscopic release.

In the preferred embodiment, the probe 36 is fabricated from a plastic that is sterilizable, e.g. Ultem or the like polymer. In an alternative embodiment, the probe 36 is fabricated from a metallic material.

As shown in the blade assembly 20a embodiment illustrated in close-up view of FIG. 2 and transverse cross-sectional view of FIG. 4A, the blade assembly 20a is configured for use on the right hand of a patient. In this embodiment, the cutting blade 16 elevates through the aperture 24 at an angle $C_{BA}$ (FIG. 4A) toward the ulnar side 28 with respect to a vertical axis $A_{BE}$ that is both perpendicular to the generally flat palmar surface 22 of the probe 36, and intersects the longitudinal axis $E_{LA}$ of the endoscope 18 (see also FIG. 5). This blade angle $C_{BA}$ is shown in FIG. 4A in a preferred orientation of approximately 20 degrees, but may range from 1 degree to 45 degrees or more. The greater the blade angle $C_{BA}$, the further the cutting blade 16 is positioned in the ulnar direction, away from the median nerve 48.

Figure 3:
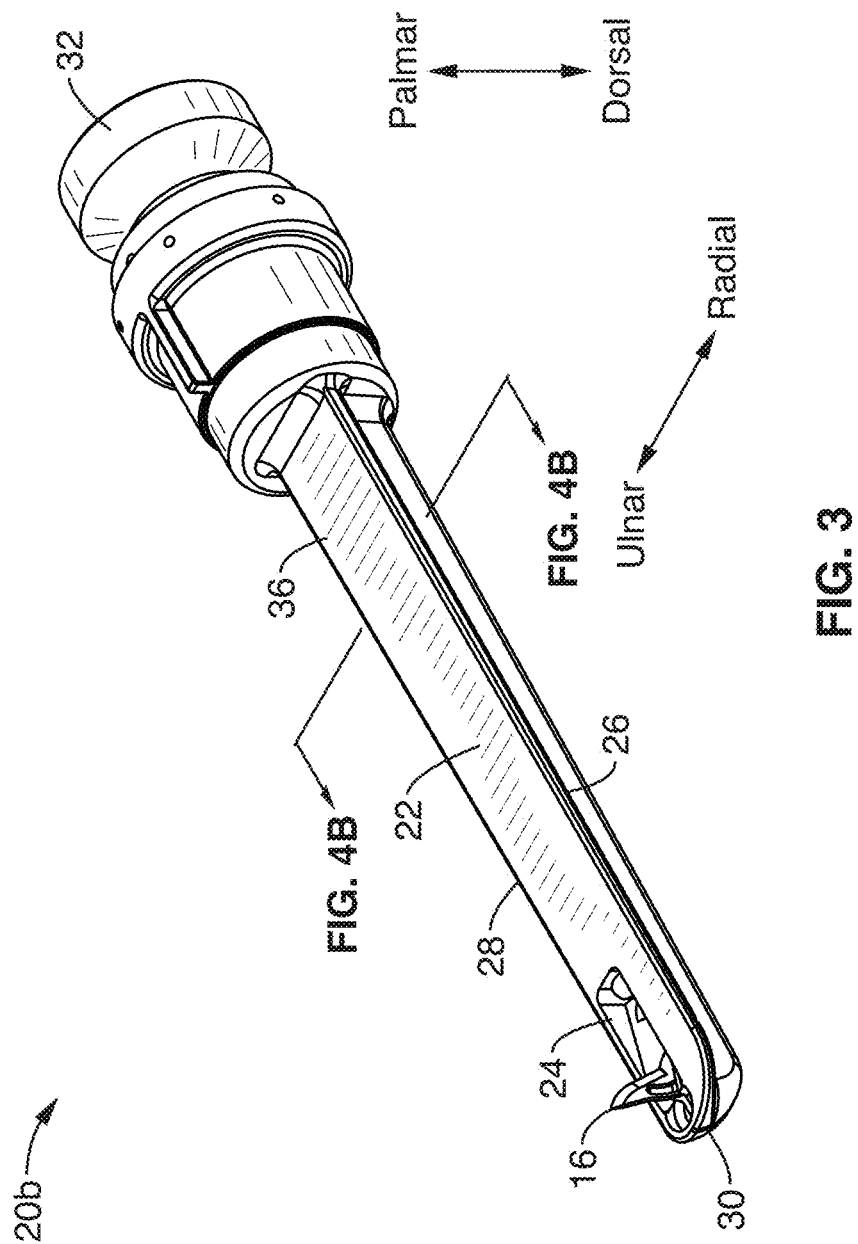
FIG. 3 is a perspective view of one embodiment of an endoscopic surgical instrument for performing ECTR using a cutting blade for elevation in a palmar-ulnar direction and a radial ledge, for use on the left hand of a patient during ECTR.
Figure 4B:
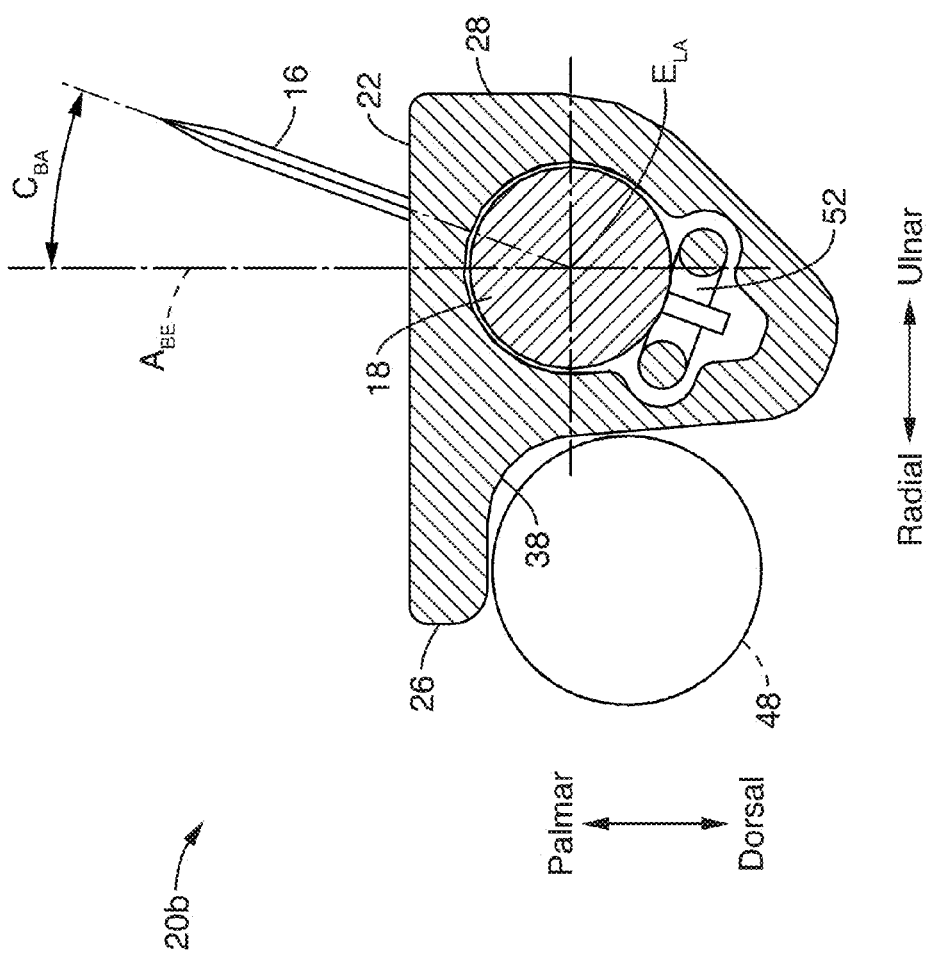
FIG. 4B is a transverse cross-sectional view of the probe shown in FIG. 3.

Referring now to the close-up view of FIG. 3 and section view of FIG. 4B, a similar blade assembly 20b is shown for use on the left hand of a patient. The difference between the blade assembly 20a for a right hand versus the blade assembly 20b for a left hand is that the cross-sectional profile of the probe body 36 is rotated 180 degrees about the vertical axis $A_{BE}$ that is both perpendicular to the flat palmar surface 22 of the probe body 36, and intersects the longitudinal axis $E_{LA}$ of the endoscope 18. The cross-sectional shape of the probe 36 for both blade assemblies 20a and 20b preferably comprises a ledge 26 on the radial side. The asymmetric shape of the probe 36 ensures that the ledge 26 is adjacent to and at least partially cups the patient's median nerve 48, thereby positioning the nerve 48 against the lower surface 38 (which encompasses both dorsal and radial surfaces) of the ledge 26 to at least partially cup the median nerve 48. As a result, the ledge 26 acts to relatively retard and/or prevent the median nerve 48 from translating across the palmar surface 22 of the probe body 36 and entering or nearing the aperture 24 where the cutting blade 16 resides. Both the ledge 26 and blade angle $C_{BA}$ provide safety features to prevent the median nerve 48 from being accidentally cut during ECTR surgery.

As shown in FIG. 1 through FIG. 4B, the blade 16 and/or the aperture 24 are offset from the radial side (i.e. ledge 26) as a result of the extent blade angle $C_{BA}$, the extent of extension of the ledge 26 laterally in the radial direction, or preferably a combination of both. It is appreciated that a smaller angle $C_{BA}$ (e.g. 0 degrees) may be used based on a larger offset as a result of extension of ledge 26 in the radial direction. Correspondingly, little or no ledge 26 may be needed with a larger blade angle $C_{BA}$.

Figure 5:
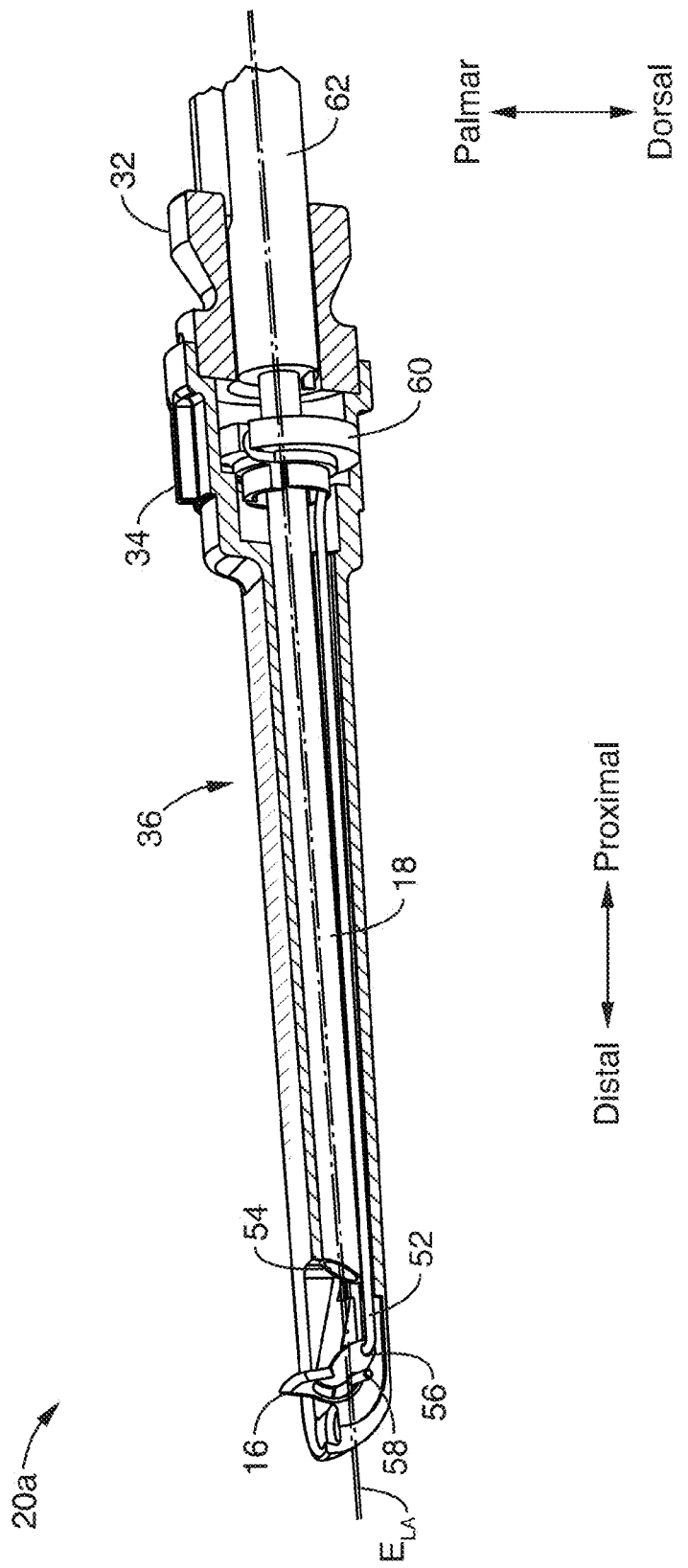
FIG. 5 is a longitudinal cross-sectional view of the probe shown in FIG. 2.

FIG. 5 shows a longitudinal cross-sectional view of the blade assembly 20a. Blade assembly 20a may comprise a proximal coupling 32 to engage with section 62 of endoscope 18. Blade operating mechanism 52 generally comprises a rod that is coupled to the blade at pivot 56, which in cooperation with pin 58, guides the blade 16 through its articulation outward and inward from the aperture 24.

Figure 6:
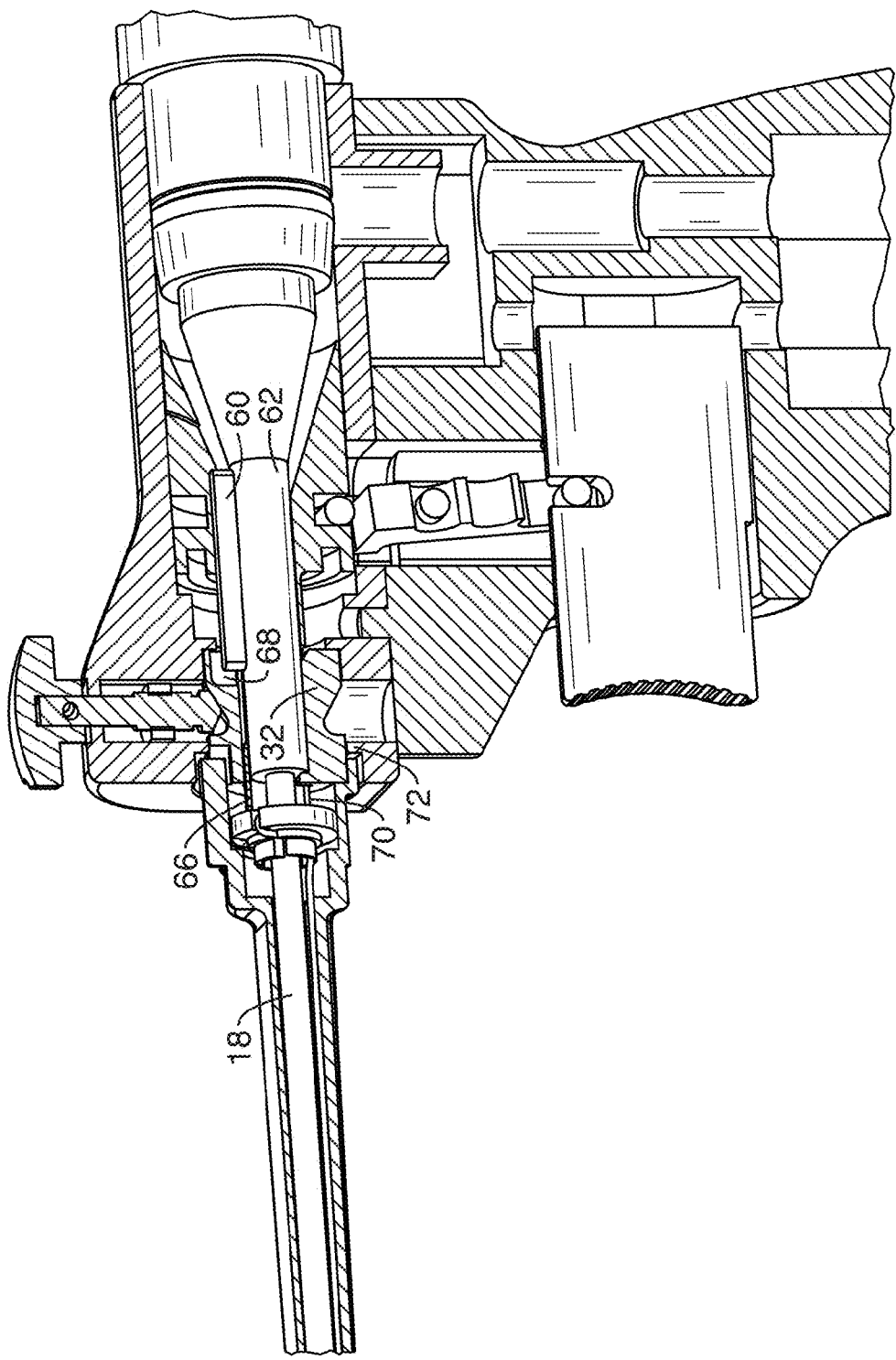
FIG. 6 is a longitudinal cross-sectional view of the endoscopic surgical instrument of FIG. 1

Rotation of the blade assembly 20a may also be visually referenced via flap 34 and corresponding collar element 60 of the endoscope 18. As shown in FIG. 6, rotation of the blade assembly 20a may also be keyed to the endoscope via palmar slot 68 and corresponding palmar rib element 60 of the endoscope 18. Rotation of the blade assembly 20a may also be keyed to the endoscope 18 via both dorsal rib element 72 and corresponding dorsal slot section 62 (not shown) of the endoscope 18 and inner slot 70 of the blade mechanism pusher 66.

Figure 7:
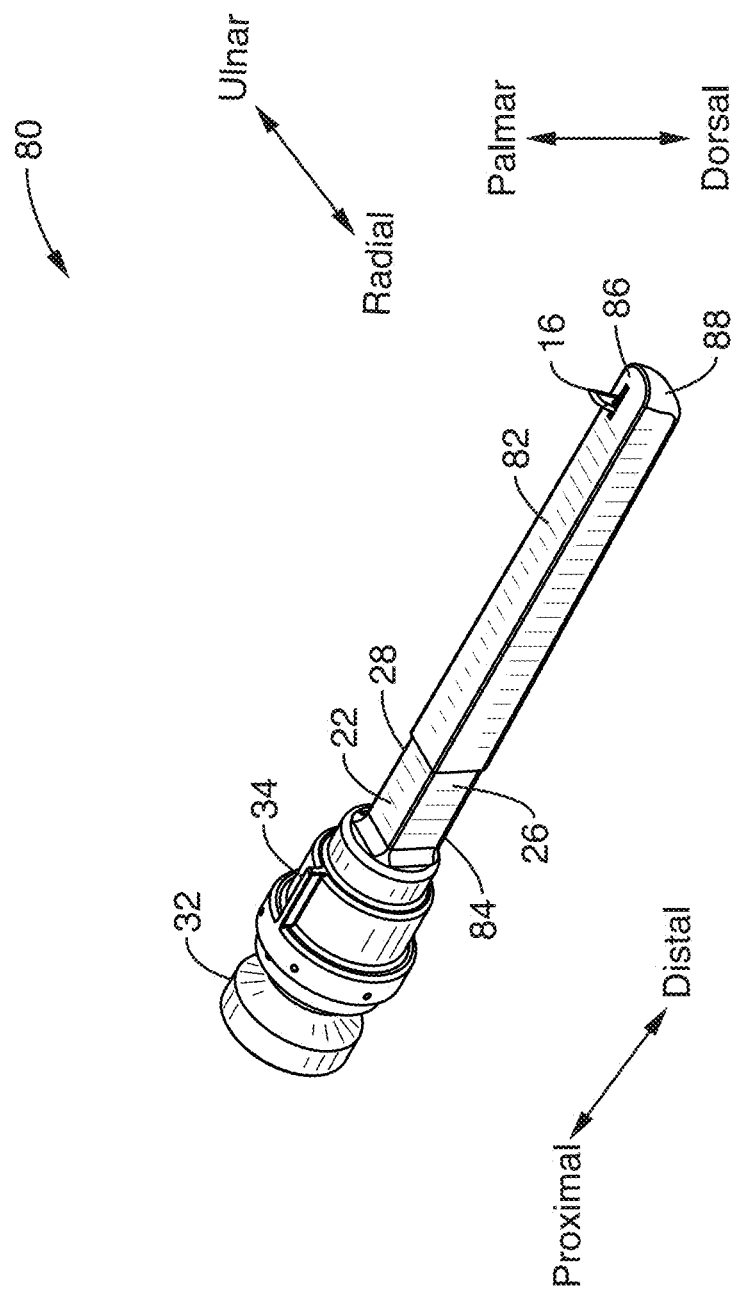
FIG. 7 is a perspective view of another embodiment of a probe with a transparent sleeve covering the aperture.

FIG. 7 shows another embodiment of a blade assembly 80 for use with an endoscopic surgical instrument 10 for dividing the flexor retinaculum. The probe 84 body in this embodiment has a sleeve 82 that is slidably received over the probe 84. The sleeve 82 is a thin, hollow, and optically transparent commercially available heat shrinkable material that is open at its proximal and distal ends, enabling it to slide from distal to proximal over the probe 84. Once inserted over the probe 84, the sleeve 82 may be heated by radiant or convection heating to shrink the sleeve 82 such that it conforms to the shape of the four surfaces of the probe 84 (palmar surface 22, dorsal surface, radial surface 26, and ulnar surface 28).

In addition, the sleeve 82 may be made of a non-distorting and optically clear transparent material that allows viewing by the endoscope 18 (FIG. 5) through the aperture 24 (FIG. 2) in the palmar surface 22 at the distal end 88 of the probe 84. Once the probe 84 is inserted into the carpal tunnel of a patient and positioned against the deep surface of the flexor retinaculum, elevation and retraction of the cutting blade 16 is performed using a similar blade elevation mechanism shown in previous figures. Once the cutting blade 16 is elevated through the aperture 24, the cutting blade 16 pierces the palmar surface of the sleeve 82, creating a slit 86 at the distal end 88 of the probe 84. In another embodiment, the slit 86 in the palmar surface of the sleeve 82 exists prior to elevation of the cutting blade 16 so that the cutting blade 16 passes through a pre-cut slit 86.

An optically clear sleeve 82 that shields the open aperture 24 (FIG. 2) prevents translation of the median nerve, and other contents of the carpal tunnel, into the aperture 24, thereby reducing the potential for injury to the median nerve during ECTR surgery. In addition, a sleeve 82 prevents fluids inside the carpal tunnel from contacting the viewing lens 54 (FIG. 5) of the endoscope 18 and distorting or obstructing the image of the contents of the carpal tunnel. By separating the dry, cooler air environment surrounding the viewing lens 54 of the endoscope 18 from the moist, warmer environment within the carpal tunnel, the sleeve 82 also reduces the potential for condensation to form on the viewing lens 54, thereby reducing the incidence and/or severity of fogging that often occurs on the viewing lens 54 when performing ECTR surgery. The sleeve 82 also traps the heat generated by the light from the endoscope, causing the air temperature inside the probe 84 to increase, thereby elevating the dew point and further reducing the potential for fogging of the viewing lens 54 with a secondary loss of image resolution from the endoscope 18 during the surgical procedure.

Figure 8:
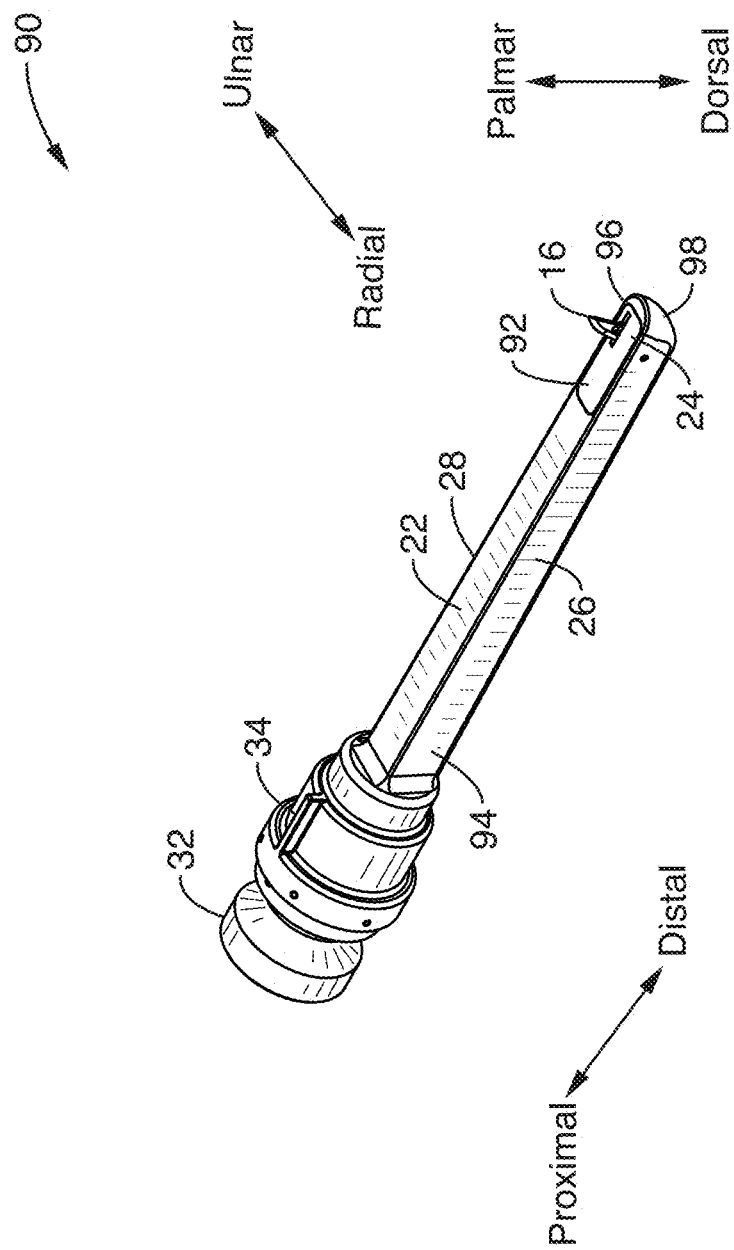
FIG. 8 is a perspective view of another embodiment of a probe with a transparent endoscopic viewing window designed into the aperture.

FIG. 8 shows another embodiment of a blade assembly 90 for use with an endoscopic surgical instrument 10 for dividing the flexor retinaculum. The probe 94 in this embodiment has a window 92 that is inserted into the aperture 24 (FIG. 2) on the palmar surface 22 of the distal end 98 of the probe 94. The window 92 may be bonded to a shallow ledge (not shown) within the aperture 24, or via other attachment means. The window 92 is preferably made of a non-distorting and optically clear transparent material that allows viewing by the endoscope 18 (FIG. 5) through the window 92. Once the probe 94 is inserted into the carpal tunnel of a patient and positioned against the deep surface of the flexor retinaculum, elevation and retraction of the cutting blade 16 is performed using a similar blade elevation mechanism shown in previous figures. As the cutting blade 16 is elevated through the aperture 24, the cutting blade 16 extends through either a pre-cut slit or creates its own slit 96 in the palmar surface of the window 92 at the distal end 98 of the probe 94.

Figure 9:
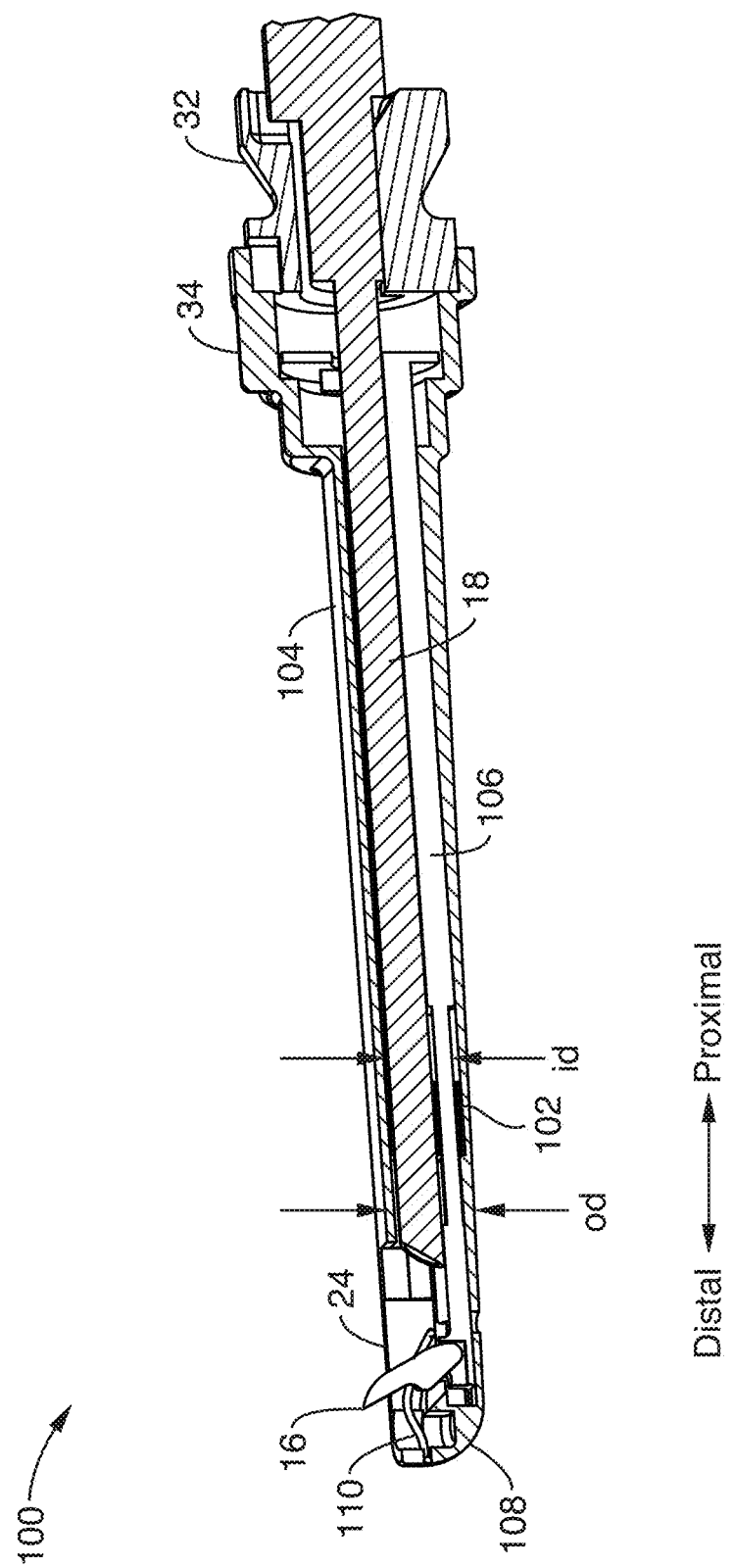
FIG. 9 is a longitudinal cross-sectional view of another embodiment of a probe with a pressure seal that conforms to both the endoscope and blade operating mechanism.
Figure 10:
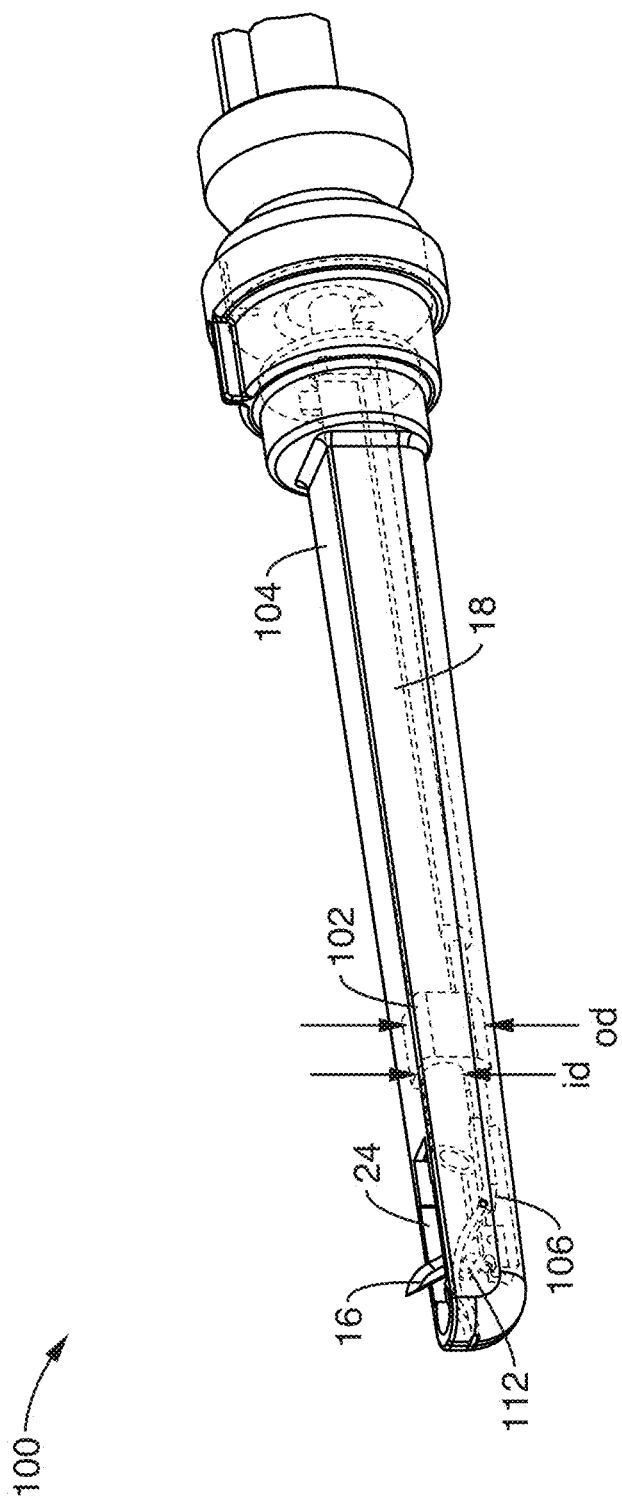
FIG. 10 is a transparent perspective view of the probe shown in FIG. 9.

FIG. 9 and FIG. 10 show another embodiment of a blade assembly 100 for use with an endoscopic surgical instrument 10 for dividing the flexor retinaculum. The increased pressure that exists within the carpal tunnel provides the driving force to translate the median nerve across the aperture 24 of the probe 104. Because the aperture 24 of the probe 104 has a direct internal path along its longitudinal length to the ambient pressure inside the operating room, a pressure gradient may exist between the aperture 24 inside the carpal tunnel (higher pressure) and the ambient pressure within the operating room (lower pressure). This pressure gradient may cause the tissues within the patient's carpal tunnel, specifically the median nerve, to be drawn into the aperture 24 where the cutting blade 16 resides. The probe 104 in this embodiment comprises a seal 102 that provides a barrier to separate the higher-pressure environment within the carpal tunnel from the lower-pressure environment within the operating room. In this embodiment, the seal 102 may comprise an elastic material that fits within the probe 104 at a location proximal to the aperture 24. The outside dimension (OD) of the seal 102 provides an interference fit with the internal dimension of the longitudinal passageway of the probe 104 where the endoscope 18 and blade operating mechanism 106 traverse from the proximal end to distal end.

The seal 102 preferably comprises two longitudinal thru holes to provide passage of the endoscope 18 and blade operating mechanism 106 from proximal to distal. Because the endoscope 18 and blade operating mechanism 106 are configured to translate proximal and distal, the compliance of the material of the seal 102 is sufficient to both enable proximal and distal movement while still maintaining a tight fit between the seal 102 and the endoscope 18 and blade operating mechanism 106. As shown in FIG. 9 and FIG. 10, distal end 108 of the probe 104 may comprise a strut 110 that guides motion of the blade 16 via pin 112 upon reciprocation of the blade operating mechanism 106.

Figure 11:
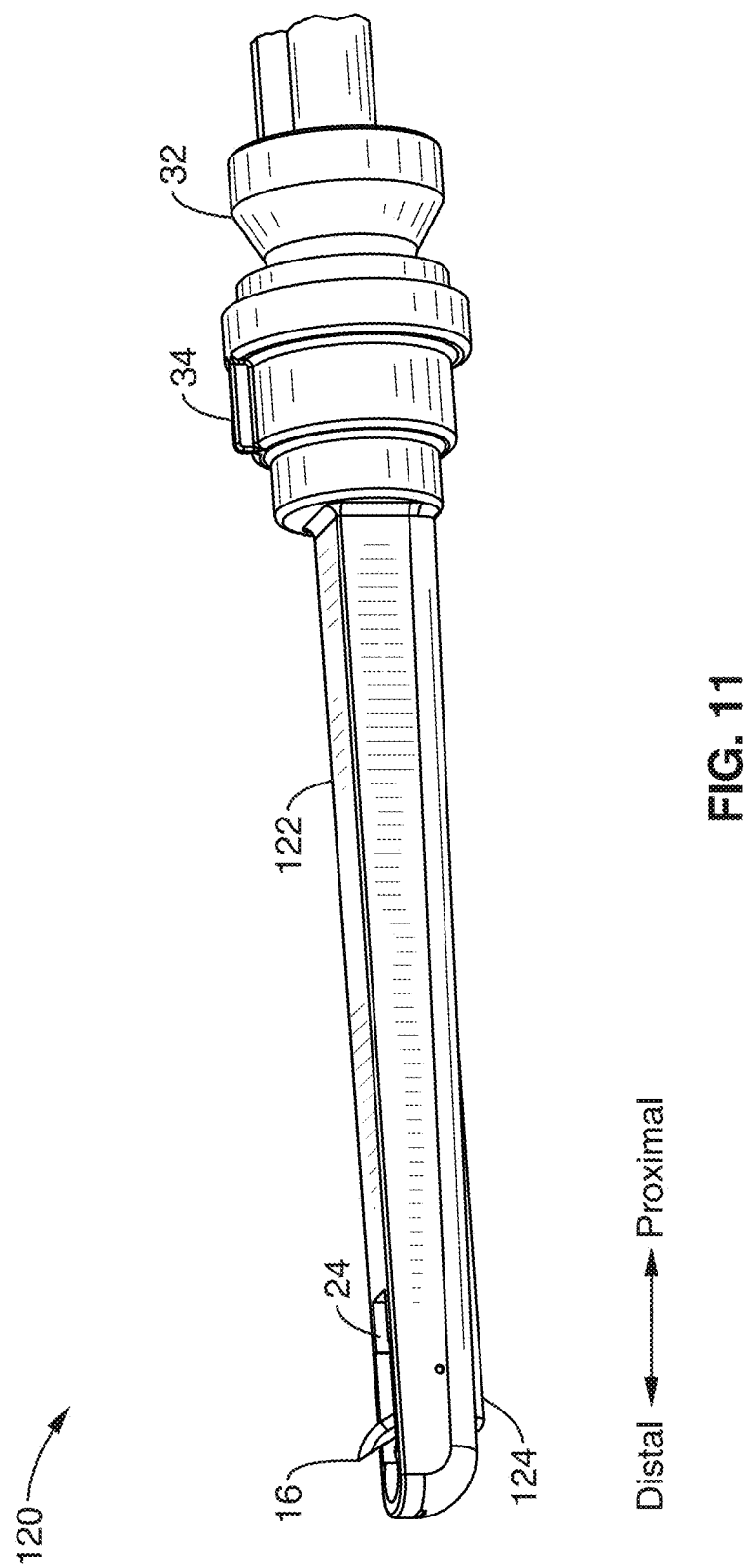
FIG. 11 is a perspective view of another embodiment of a probe with a pressure O-ring that conforms to the endoscope.
Figure 12:
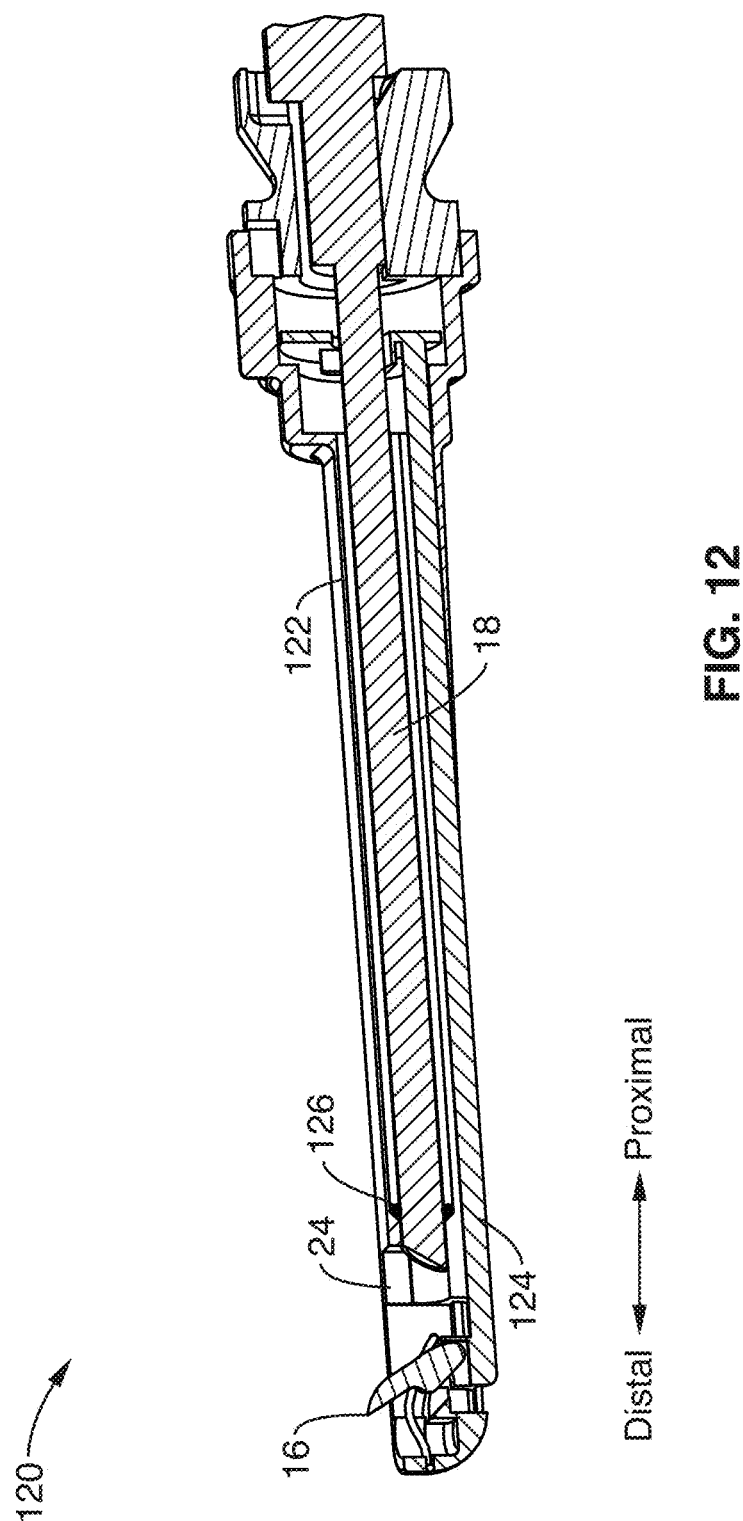
FIG. 12 is a longitudinal cross-sectional view of the probe shown in FIG. 11.

FIG. 11 and FIG. 12 show an alternative embodiment of a blade assembly 120 for separating the higher-pressure environment within the carpal tunnel from the lower-pressure environment within the operating room. In this embodiment, the endoscope 18 passes from proximal to distal through the longitudinal bore of the probe 122 and uses an O-ring seal 126 to provide the barrier around the endoscope 18. The blade operating mechanism 124 is mounted external to the longitudinal bore of the probe 122 and therefore does not require a sealing means, since it does not provide a fluid or air path between the higher-pressure environment within the carpal tunnel and the lower-pressure environment within the operating room.

Figure 13A:
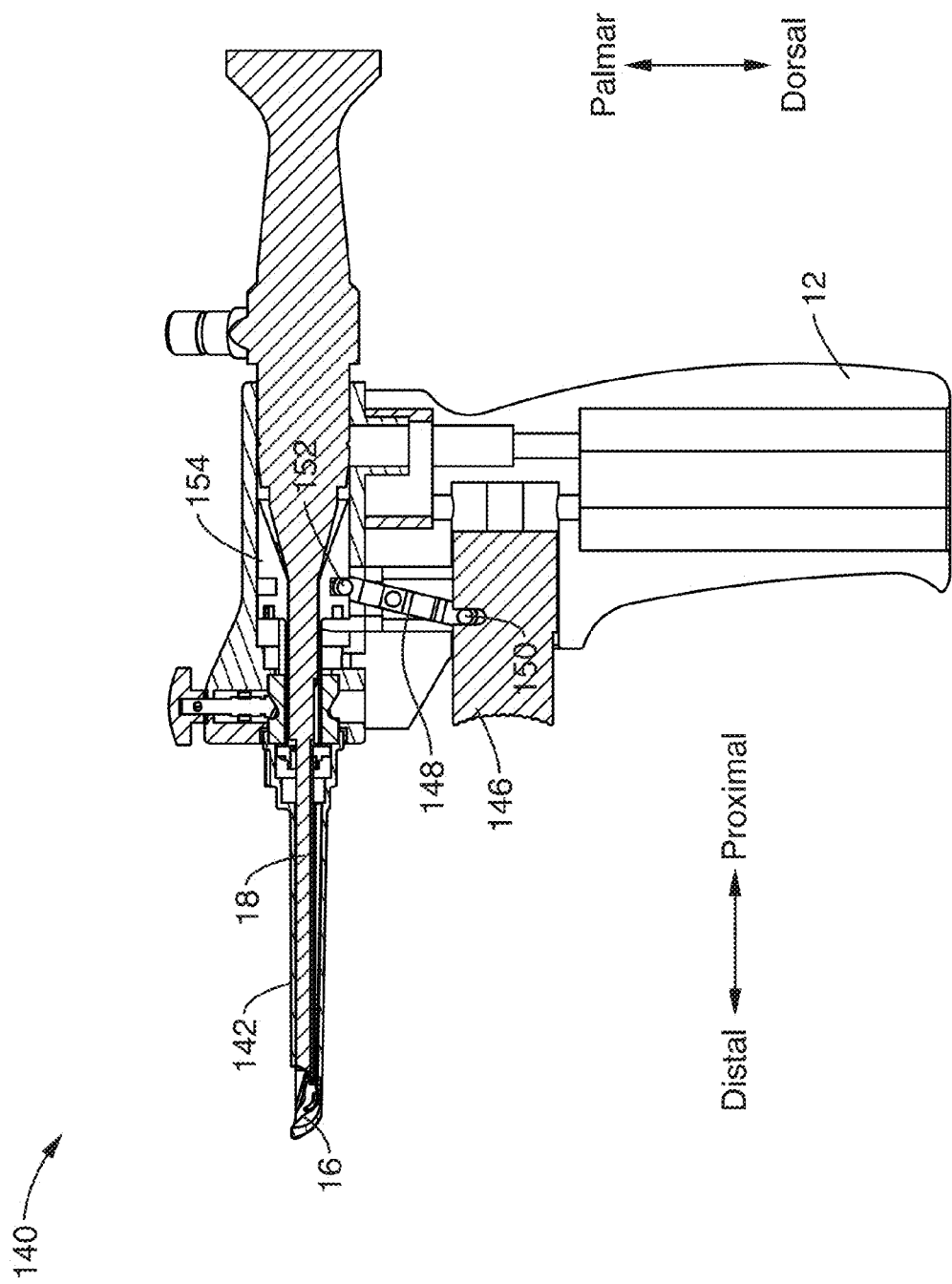
FIG. 13A is a longitudinal cross-sectional view of another embodiment of an endoscopic surgical instrument with a translating endoscope, shown with the blade retracted.
Figure 13B:
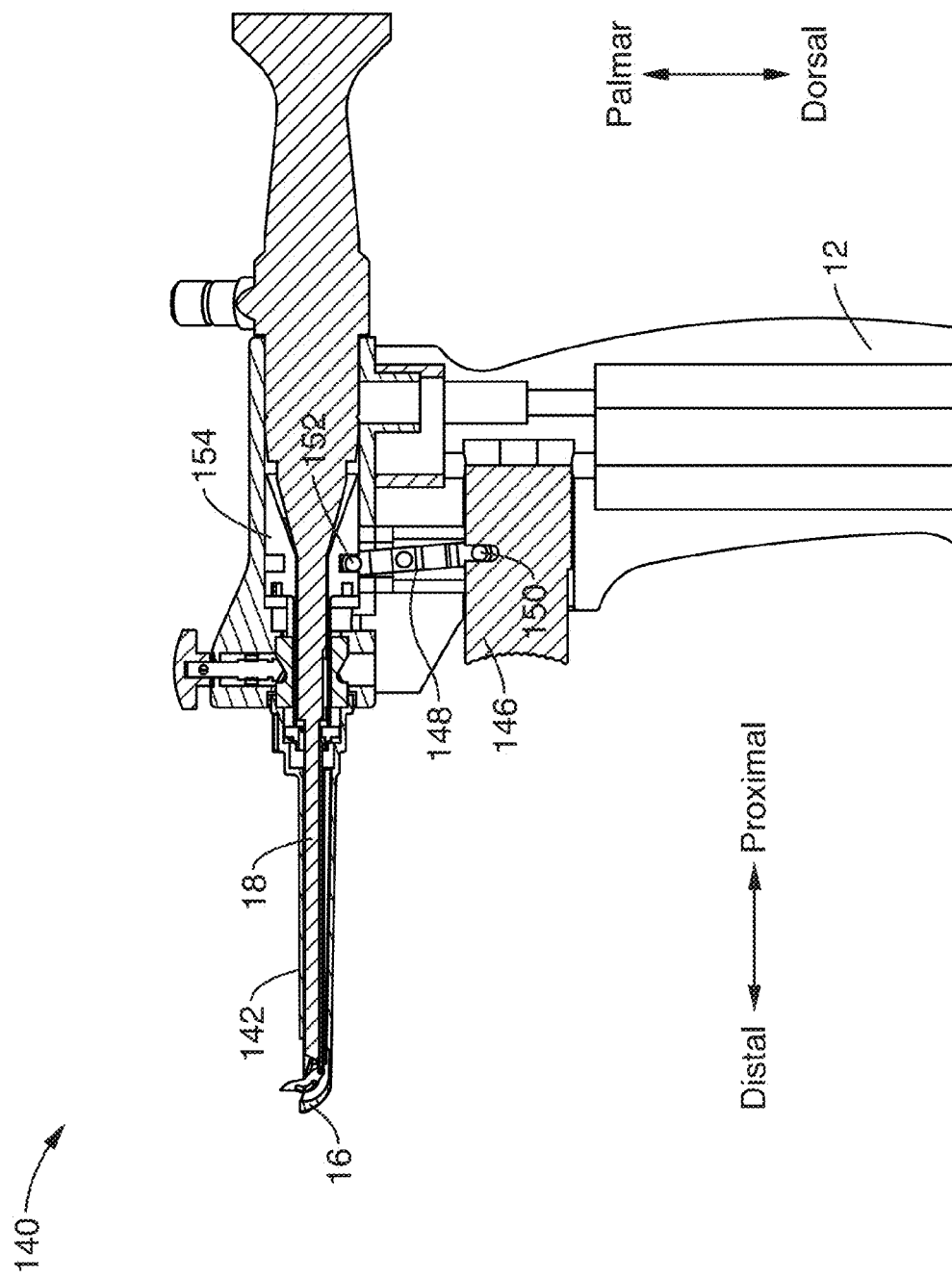
FIG. 13B is a longitudinal cross-sectional view of the endoscopic surgical instrument of FIG. 13A shown with the blade elevated.

FIG. 13A and FIG. 13B show an alternative embodiment of an endoscopic surgical instrument 140 for dividing the flexor retinaculum. In this embodiment, the endoscope 18 translates from a proximal position (FIG. 13A) to a distal position (FIG. 13B) when the blade elevation trigger 146 is depressed from distal to proximal by the surgeon. By translating the endoscope 18 distally as the cutting blade 16 is repositioned from its retracted position within the probe 142 (FIG. 13A) to its elevated position (FIG. 13B), the viewing lens 54 (FIG. 5) of the endoscope 18 is repositioned nearer the cutting blade 16 to provide a magnified image on the video monitor (not shown). This provides the surgeon with improved viewing while dividing the flexor retinaculum, and as a visual alert that the cutting blade 16 is elevating to either cut the flexor retinaculum or injure the median nerve, depending on the degree of apposition of the aperture 24 to the deep side of the flexor retinaculum. One end of a pivot link 148 inserts into a slot 150 in the blade elevation trigger 146. The opposite end of the pivot link 148 inserts into a cylindrical groove 152 in the translator mechanism 154. As the blade elevation trigger 146 is depressed, the pivot link 148 rotates counter-clockwise, moving the translator mechanism 154. The translator mechanism 154 is slidably received on and secured to the longitudinal shaft of the endoscope 18 in a distal direction. When the blade elevation trigger 146 is released, the pivot link 148 rotates clockwise, moving the translator mechanism 154 and endoscope 18 in a proximal direction.

Figure 14:
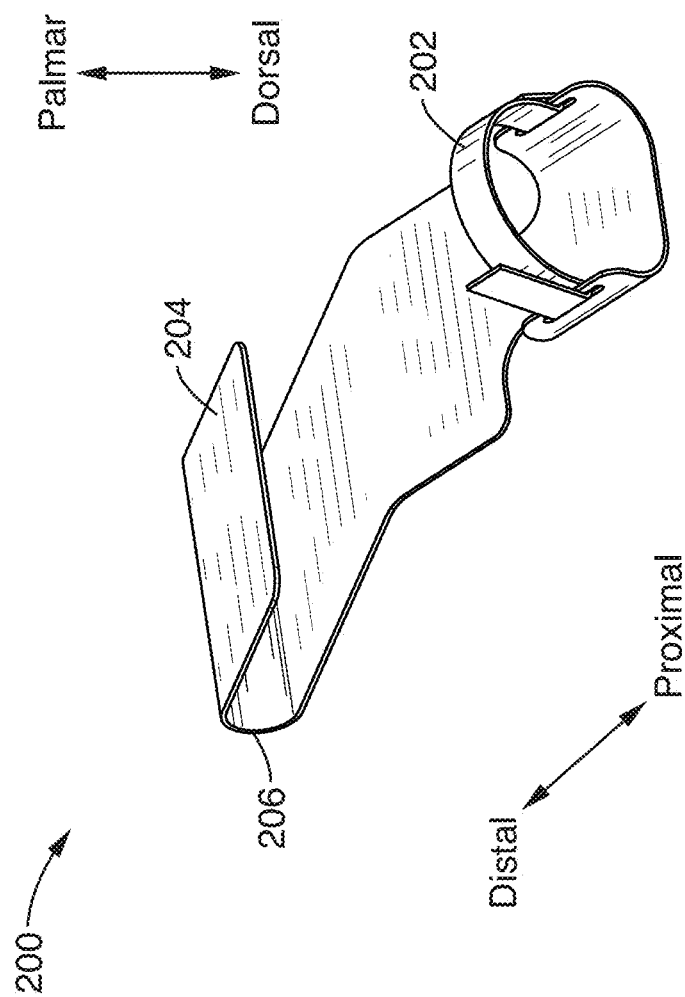
FIG. 14 is a perspective view of a finger extension clamp in accordance with the systems and methods of the present description.

FIG. 14 shows one embodiment of a finger extension clamp 200. If the patient flexes their fingers while the surgeon is performing endoscopic surgery for CTS, the lumbrical muscles move from distal to proximal, entering the carpal tunnel. Consequently, the pressure within the carpal tunnel increases. If the patient then grips forcefully, the lumbrical muscles contract, causing the pressure within the carpal tunnel to increase significantly more. This increase in pressure acts to create a pressure differential that will translate the median nerve across the margins of the aperture of the endoscopic surgical instrument, increasing the risk of injury to the median nerve if the cutting blade is elevated. The finger extension clamp 200 minimizes the angle of flexion of the patient's fingers at all three joints of each finger (distal interphalangeal joints, proximal interphalangeal joints, and metacarpophalangeal joints), at the time of surgery. This minimizes the pressure differential that can cause the median nerve to translate into the path of the elevating cutting blade and/or the cutting blade's proximal translation during the withdrawal maneuver for division of the flexor retinaculum.

In a preferred embodiment, the finger extension clamp 200 comprises a plastic sheet material that easily conforms to the dorsal side of the patient's forearm, wrist, and hand. At the proximal end of the finger extension clamp 200 is a strap 202 that secures the finger extension clamp 200 to the patient's forearm, proximal to their wrist. At the distal end of the finger extension clamp 200 is a U-shaped bend 206 that forms the palmar clamp 204, which secures the patients fingers and limits them from flexing.

Figure 15:
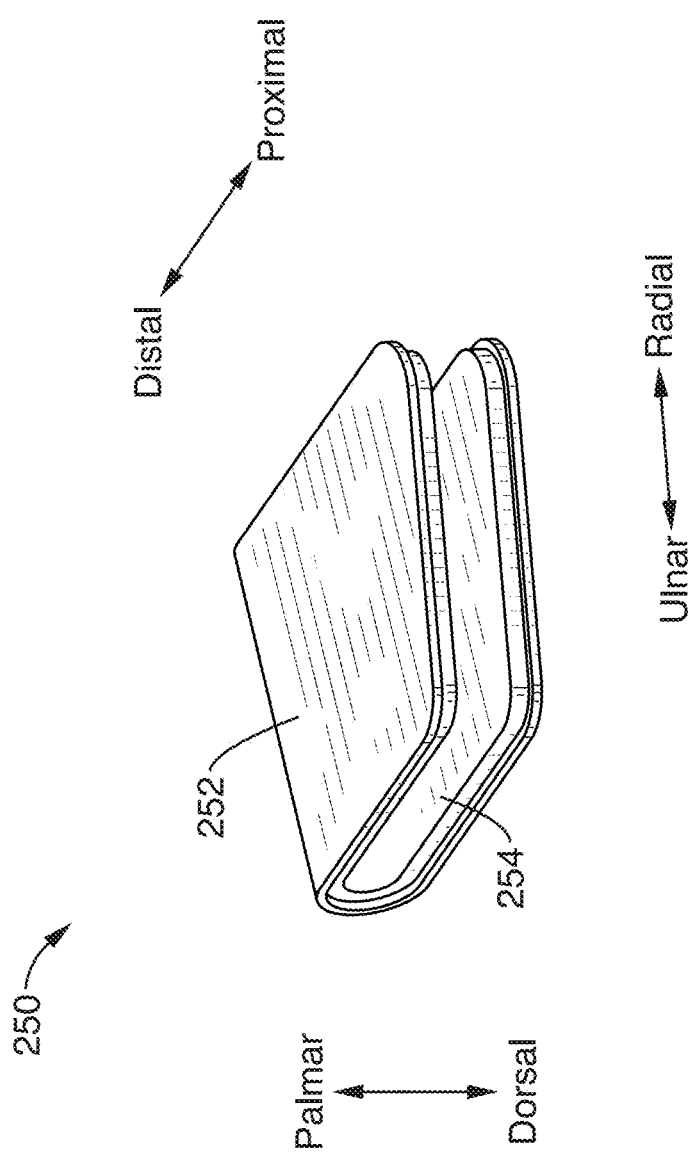
FIG. 15 is a perspective view of another embodiment of a finger extension clamp in accordance with the systems and methods of the present description.

FIG. 15 shows another embodiment of a finger extension clamp 250. In this embodiment, the finger extension clamp minimizes the patient's fingers from flexing at their distal and proximal interphalangeal joints, leaving the metacarpophalangeal (MCP) joints free to flex. The finger extension clamp 250 comprises a rigid outer layer 252 made from a polymeric (e.g. plastic) sheet material (or similar suitable rigid material) and an inner layer 254 made from a compliant foam, rubber or like material. The inner layer 254 aids in distributing the clamping force over all the fingers and provides the friction needed to prevent the finger extension clamp 250 from sliding off of the fingers. The finger extension clamp 250 is U-shaped and slides over the distal end of the patient's four fingers until the proximal end is just distal to the MCP joints of the fingers. When not installed on the patient's fingers, the dorsal and palmar surfaces of the outer layer 252 are preferably substantially parallel. When installed over the patient's fingers, the proximal end of the finger extension clamp 250 opens to conform to the tapered profile of the patient's fingers. The proximal end of the finger extension clamp 250 is preferably tapered from radial to ulnar to conform to the shape of the MCP joints. By rotating the finger extension clamp 250, it can be used on either the left or right hand of the patient. This finger extension clamp 250 enables the surgeon to palpate the palm of the patient's hand both over the carpal tunnel and just distal to it.

From the description herein, it will be appreciated that that the present disclosure encompasses multiple embodiments which include, but are not limited to, the following:

1. An apparatus for treating a flexor retinaculum for carpal tunnel release surgery within a patient, the apparatus comprising: an elongate probe body comprising a longitudinal axis terminating at a distal end, and a radial surface and palmar surface both extending proximally from the distal end; wherein the elongate probe body is configured to be inserted in a carpal tunnel of the patient such that the radial surface is positioned adjacent a median nerve of the patient; an aperture disposed in the probe body within the palmar surface at a location near the distal end; and a cutting blade disposed within the aperture; wherein the cutting blade is coupled to the probe body such that it is configured to reciprocate from a retracted position within the aperture to an extended position extending outward from the palmar surface; and wherein the cutting blade extends into the extended position in a plane that is offset from the longitudinal axis away from the radial surface toward the ulnar surface.

2. The apparatus of any preceding embodiment, wherein the cutting blade is positioned within the aperture such that the cutting blade extends from the aperture at a plane that is at an angle with respect to a vertical axis that is perpendicular to either the palmar surface or longitudinal axis of the probe body.

3. The apparatus of any preceding embodiment, wherein the angle is within a range between approximately 1 degree and 45 degrees.

4. The apparatus of any preceding embodiment, wherein the greater the angle within the range, the further the cutting blade is positioned toward the ulnar surface and away from the radial surface and median nerve.

5. The apparatus of any preceding embodiment, wherein the palmar surface comprises a ledge extending from the radial surface.

6. The apparatus of any preceding embodiment: the probe body further comprising a dorsal surface adjacent the radial surface and extending parallel to the longitudinal axis proximally from the distal end; wherein the ledge forms a lower surface that encompasses at least a portion of the dorsal surface and radial surface of the ledge to at least partially cup the median nerve when the probe body is inserted in the carpal tunnel.

7. The apparatus of any preceding embodiment, wherein the ledge acts to separate the median nerve from the cutting blade to prohibit the median nerve from translating across the palmar surface of the probe body and entering or nearing the aperture.

8. The apparatus of any preceding embodiment, further comprising: a blade operating mechanism coupled to the blade for selectively and incrementally extending and retracting the cutting blade out of and back into the aperture.

9. The apparatus of any preceding embodiment, further comprising: an optical system inserted within the probe body along said longitudinal axis; said optical system having a distal portion terminating adjacent a proximal end of the aperture, thereby defining a viewing space between the distal portion of the optical system and a distal end of the aperture; wherein the cutting blade extends from the viewing space through the aperture.

10. The apparatus of any preceding embodiment, wherein the aperture is covered with a substantially transparent material.

11. The apparatus of any preceding embodiment, wherein the substantially transparent material comprises a sleeve that is shrink-fit to the probe body.

12. The apparatus of any preceding embodiment, wherein the substantially transparent material comprises a window that is inserted onto a surface of the aperture.

13. The apparatus of any preceding embodiment, further comprising a longitudinal slit within the substantially transparent material to allow extension of the cutting blade.

14. The apparatus of any preceding embodiment, wherein the cutting blade forms the longitudinal slit when it is extended through the aperture.

15. The apparatus of any preceding embodiment, wherein the optical system is coupled to the blade operating mechanism such that operation of the blade operating mechanism translates the distal portion of the optical system distally within the aperture when extending the cutting blade.

16. The apparatus of any preceding embodiment, wherein the distal translation of the optical system provides magnification of the viewing space during treatment.

17. An apparatus for treating a flexor retinaculum for carpal tunnel release surgery within a patient, the apparatus comprising: an elongate probe body comprising a longitudinal axis terminating at a distal end, and a radial surface and palmar surface both extending proximally from the distal end; wherein the elongate probe body is configured to be inserted in a carpal tunnel of the patient such that the radial surface is positioned adjacent a median nerve of the patient; an aperture disposed in the probe body within the palmar surface at a location near the distal end; and a cutting blade disposed within the aperture; wherein the cutting blade is coupled to the probe body such that it is configured to reciprocate from a retracted position within the aperture to an extended position extending outward from the palmar surface; wherein the aperture is covered with a substantially transparent material.

18. The apparatus of any preceding embodiment, wherein the substantially transparent material comprises a sleeve that is shrink-fit to the probe body.

19. The apparatus of any preceding embodiment, wherein the substantially transparent material comprises a window that is inserted onto a surface of the aperture.

20. The apparatus of any preceding embodiment, further comprising a longitudinal slit within the substantially transparent material to allow extension of the cutting blade.

21. The apparatus of any preceding embodiment, wherein the cutting blade forms the longitudinal slit when it is extended through the aperture.

22. An apparatus for treating a flexor retinaculum for carpal tunnel release surgery within a patient, the apparatus comprising: an elongate probe body comprising a longitudinal axis terminating at a distal end, and a radial surface and palmar surface both extending proximally from the distal end; wherein the elongate probe body is configured to be inserted in a carpal tunnel of the patient such that the radial surface is positioned adjacent a median nerve of the patient; an aperture disposed in the probe body within the palmar surface at a location near the distal end; and a cutting blade disposed within the aperture; wherein the cutting blade is coupled to the probe body such that it is configured to reciprocate from a retracted position within the aperture to an extended position extending outward from the palmar surface; a blade operating mechanism coupled to the blade for selectively and incrementally extending and retracting the cutting blade out of and back into the aperture; an optical system inserted within the probe body along said longitudinal axis; said optical system having a distal portion terminating adjacent a proximal end of the aperture, thereby defining a viewing space between the distal portion of the optical system and a distal end of the aperture; wherein the cutting blade extends from the viewing space through the aperture; wherein one or more of the optical system and blade operating mechanism is disposed in a channel running along the longitudinal axis from a proximal end of the probe body to the aperture; and a seal disposed in the channel for preventing the flow of air or fluid from distal to proximal within the channel.

23. The apparatus of any preceding embodiment, wherein the seal prevents or reduces the flow of air or fluid from the aperture to the proximal end of the probe body along the longitudinal length of one or more of the optical system and blade operating mechanism.

24. The apparatus of any preceding embodiment, wherein the seal provides a barrier to separate the higher-pressure environment within the carpal tunnel from a lower-pressure environment within the operating room.

25. A probe for a surgical instrument used for cutting the flexor retinaculum while under endoscopic visual inspection, the probe comprising: (a) a proximal end connectable to a surgical hand piece, wherein the proximal end is open so as to allow passage of an optical system and a cutting blade extension system; (b) a distal end, wherein the distal end is closed; and (c) a hollow length extending from the proximal end to the distal end, the hollow length comprising: a flat top surface with a lateral aperture near the distal end through which a cutting blade can be extended and retracted under operation of the cutting blade extension system while visualizing tissue at the lateral aperture with the optical system, wherein the cutting blade extends from the aperture at an angle to a vertical axis that is both perpendicular to the flat top surface of the probe and intersects the longitudinal axis of the optical system, the flat top surface having a width dimension spanning a distance from a radial side to an ulnar side of the flat top surface, wherein the distance from a vertical axis that is both perpendicular to the flat top surface of the probe and intersects the longitudinal axis of the optical system to the edge of the radial side is greater than the distance from the vertical axis to the ulnar side, a lower surface connected to the radial side and ulnar side of the flat top surface, wherein the lower surface is sized to permit passage of an optical system and a cutting blade extension system between the flat top surface and the lower surface, the lower surface having a width dimension spanning a distance from the radial side to the ulnar side, wherein the distance from a vertical axis that is both perpendicular to the flat top surface of the probe and intersects the longitudinal axis of the optical system to the edge of the radial side is greater than the distance from the vertical axis to the ulnar side at all points between the flat top surface and a fixed distance below the flat top surface, whereby the fixed distance is less than or equal to the distance from the flat top surface to a horizontal axis that is both perpendicular to the vertical axis and intersects the longitudinal axis of the optical system, thereby forming a ledge on the radial side, the lower surface also having a width dimension which is equal to the width dimension of the flat top surface for a defined distance below the flat top surface, wherein the defined distance is greater than zero inches but less than 0.125 inches.

26. A method for treating a flexor retinaculum for carpal tunnel release surgery within a patient, the method comprising: providing an elongate probe body comprising a longitudinal axis terminating at a distal end, and a radial surface and palmar surface both extending proximally from the distal end; inserting the elongate probe body into in a carpal tunnel of the patient such that the radial surface is positioned adjacent a median nerve of the patient; wherein an aperture disposed in the probe body within the palmar surface at a location near the distal end is positioned adjacent the flexor retinaculum; reciprocating a cutting blade that is coupled to the probe body from a retracted position within the aperture to an extended position extending outward from the palmar surface; wherein the cutting blade extends into the extended position in a plane that is offset from the longitudinal axis away from the radial surface toward the ulnar surface; and cutting at least a portion of the flexor retinaculum with the cutting blade.

27. A method as in any of the previous embodiments, wherein cutting the flexor retinaculum comprises dividing the flexor retinaculum.

28. A method as in any of the previous embodiments, wherein the cutting blade is positioned within the aperture such that the cutting blade extends from the aperture at a plane that is at an angle with respect to a vertical axis that is perpendicular to either the palmar surface or longitudinal axis of the probe body.

29. A method as in any of the previous embodiments, wherein the angle is within a range between approximately 1 degree and 45 degrees.

30. A method as in any of the previous embodiments, wherein the greater the angle within the range, the further the cutting blade is positioned toward the ulnar surface and away from the radial surface and median nerve.

31. A method as in any of the previous embodiments, wherein the palmar surface comprises a ledge extending from the radial surface.

32. A method as in any of the previous embodiments, the probe body further comprising a dorsal surface adjacent the radial surface and extending proximally from the distal end; wherein the ledge forms a lower surface that encompasses at least a portion of the dorsal surface and radial surface of the ledge; the method further comprising cupping at least a portion of the median nerve with the lower surface when the probe body is inserted in the carpal tunnel.

33. A method as in any of the previous embodiments, further comprising: separating the median nerve from the cutting blade to prohibit the median nerve from translating across the palmar surface of the probe body and entering or nearing the aperture.

34. A method as in any of the previous embodiments, further comprising: activating a blade operating mechanism coupled to the blade for selectively and incrementally extending and retracting the cutting blade out of and back into the aperture.

35. A method as in any of the previous embodiments, the probe further comprising an optical system inserted within the probe body along said longitudinal axis; said optical system having a distal portion terminating adjacent a proximal end of the aperture, thereby defining a viewing space between the distal portion of the optical system and a distal end of the aperture; the method further comprising viewing the aperture and flexor retinaculum with the optical system while the cutting blade extends from the viewing space through the aperture.

36. A method as in any of the previous embodiments, wherein the aperture is covered with a substantially transparent material.

37. A method as in any of the previous embodiments, wherein the substantially transparent material comprises a sleeve that is shrink-fit to the probe body.

38. A method as in any of the previous embodiments, wherein the substantially transparent material comprises a window that is inserted onto a surface of the aperture.

38. A method as in any of the previous embodiments, further comprising a longitudinal slit within the substantially transparent material to allow extension of the cutting blade.

39. A method as in any of the previous embodiments, wherein the cutting blade forms the longitudinal slit when it is extended through the aperture.

40. A method as in any of the previous embodiments, wherein the optical system is coupled to the blade operating mechanism, the method further comprising: operating of the blade operating mechanism such that the distal portion of the optical system translates distally within the aperture when extending the cutting blade.

41. A method as in any of the previous embodiments, wherein the distal translation of the optical system provides magnification of the viewing space during treatment.

42. An apparatus comprising a finger extension clamp that minimizes a patient's fingers from flexing at their distal and proximal interphalangeal joints, leaving the metacarpophalangeal (MCP) joints free to flex.

43. The apparatus of any preceding embodiment, wherein the finger extension clamp comprises a u-shaped clamp having a rigid outer layer and a compliant inner layer for distributing the clamping force over all the fingers and providing friction needed to prevent the finger extension clamp from sliding off of the fingers.

44. A finger extension clamp that minimizes the angle of flexion of the patient's fingers at the distal interphalangeal joint, proximal interphalangeal joint, and metacarpophalangeal joint at the time of surgery.

45. The apparatus of any preceding embodiment, wherein the finger extension clamp comprises a strap that secures the finger extension clamp to a patient's forearm, proximal to the wrist; and a U-shaped bend at the distal end of the finger extension clamp that forms the palmar clamp that secures the patients fingers to limit them from flexing.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for treating a flexor retinaculum for carpal tunnel release surgery within a patient, the apparatus comprising:
    an elongate probe body comprising a longitudinal axis terminating at a distal end, and a radial surface and palmar surface both extending proximally from the distal end;
    wherein the elongate probe body is configured to be inserted in a carpal tunnel of the patient such that the radial surface is positioned adjacent a median nerve of the patient;
    an aperture disposed in the probe body within the palmar surface at a location near the distal end; and
    a cutting blade disposed within the aperture;
    wherein the cutting blade is coupled to the probe body such that it is configured to reciprocate from a retracted position within the aperture to an extended position extending outward from the palmar surface; and
    wherein the cutting blade extends into the extended position such that the tip of the blade in the extended position is offset away from the radial surface and toward an ulnar surface opposite the radial surface of the elongate probe body.

2. An apparatus as recited in claim 1, wherein the cutting blade is positioned within the aperture such that the cutting blade extends from the aperture at a plane that is at an angle with respect to a vertical axis that is perpendicular to the palmar surface of the probe body.

3. An apparatus as recited in claim 2, wherein the angle is within a range between approximately 1 degree and 45 degrees.

4. An apparatus as recited in claim 3, wherein the greater the angle within the range, the further the cutting blade is positioned toward the ulnar surface and away from the radial surface and median nerve.

5. An apparatus as recited in claim 1, wherein the palmar surface comprises a ledge extending from the radial surface.

6. An apparatus as recited in claim 5:
the probe body further comprising a dorsal surface adjacent the radial surface and extending proximally from the distal end;
wherein the ledge forms a lower surface that encompasses at least a portion of the dorsal surface and radial surface of the ledge to at least partially cup the median nerve when the probe body is inserted in the carpal tunnel.

7. An apparatus as recited in claim 6, wherein the ledge acts to separate the median nerve from the cutting blade to prohibit the median nerve from translating across the palmar surface of the probe body and entering or nearing the aperture.

8. An apparatus as recited in claim 1, further comprising:
a blade operating mechanism coupled to the blade for selectively and incrementally extending and retracting the cutting blade out of and back into the aperture.

9. An apparatus as recited in claim 8, further comprising:
an optical system inserted within the probe body along said longitudinal axis;
said optical system having a distal portion terminating adjacent a proximal end of the aperture, thereby defining a viewing space between the distal portion of the optical system and a distal end of the aperture;
wherein the cutting blade extends from the viewing space through the aperture.

10. An apparatus as recited in claim 9, wherein the aperture is covered with a substantially transparent material.

11. An apparatus as recited in claim 10, wherein the substantially transparent material comprises a sleeve that is shrink-fit to the probe body.

12. An apparatus as recited in claim 10, wherein the substantially transparent material comprises a window that is inserted onto a surface of the aperture.

13. An apparatus as recited in claim 10, further comprising a longitudinal slit within the substantially transparent material to allow extension of the cutting blade.

14. An apparatus as recited in claim 13, wherein the cutting blade forms the longitudinal slit when it is extended through the aperture.

15. An apparatus as recited in claim 9, wherein the optical system is coupled to the blade operating mechanism such that operation of the blade operating mechanism translates the distal portion of the optical system distally within the aperture when extending the cutting blade.

16. An apparatus as recited in claim 15, wherein the distal translation of the optical system provides magnification of the viewing space during treatment.

* * * * *